United States Patent [19]
Wise et al.

[11] Patent Number: 5,989,445
[45] Date of Patent: Nov. 23, 1999

[54] MICROCHANNEL SYSTEM FOR FLUID DELIVERY

[75] Inventors: Kensall D. Wise; Jingkuang Chen, both of Ann Arbor, Mich.

[73] Assignee: The Regents of the University of Michigan, Ann Arbor, Mich.

[21] Appl. No.: 09/098,695

[22] Filed: Jun. 17, 1998

Related U.S. Application Data

[62] Division of application No. 08/489,069, Jun. 9, 1995.

[51] Int. Cl.$^6$ .............................. H01L 21/00; B44C 1/22
[52] U.S. Cl. ................................. 216/62; 216/2; 216/27; 216/39; 216/67; 216/87; 438/734; 438/735; 438/753
[58] Field of Search .................................. 216/2, 62, 87, 216/39, 56, 27; 438/719, 734, 735, 753

[56] References Cited

U.S. PATENT DOCUMENTS

| | | | |
|---|---|---|---|
| 3,921,916 | 11/1975 | Bassous | 239/602 |
| 4,455,192 | 6/1984 | Tamai | 156/628 |
| 5,308,442 | 5/1994 | Taub et al. | 347/65 |
| 5,385,635 | 1/1995 | O'Neill | 347/65 |
| 5,585,827 | 12/1996 | Murakami | 347/65 |
| 5,588,597 | 12/1996 | Reinecke et al. | 239/533.5 |

OTHER PUBLICATIONS

"A Novel Fabrication Method of Capillary Tubes on Quartz for Chemical Analysis Applications," by Kaplan, et al., *IEEE Proceedings, Micro Electro Mechanical Systems*, Jan. 25–28, 1994.

"Silicon Processed Microneedles," by Lin, et al., *The 7$^{th}$ International Conference on Solid State Sensors and Actuators*; Jun. 7–10, 1993.

*Primary Examiner*—Bruce Breneman
*Assistant Examiner*—Alva C Powell
*Attorney, Agent, or Firm*—Rader, Fishman & Grauer PLLC

[57] ABSTRACT

Microchannels for conducting and expelling a fluid are embedded in a surface of a silicon substrate. A channel seal is made of plural cross structures formed integrally with the silicon substrate. The cross structures are arranged sequentially over each channel, each cross structure having a chevron shape. The microchannel is sealed by oxidizing at least partially the cross structures, whereby the spaces therebetween are filled. A dielectric seal which overlies the thermally oxidized cross structures forms a complete seal and a substantially planar top surface to the silicon substrate. The dielectric seal is formed of a low pressure chemical vapor deposition (LPCVD) dielectric layer. The channel is useful in the production of an ink jet print in head, and has a polysilicon heater overlying the dielectric seal. A current passing through the heater causes a corresponding increase in the temperature of the ink in the microchannel, causing same to be expelled therefrom. After expulsion of the fluid, the microchannel is refilled by capillary action. Control circuitry, including bonding pads and sensors, can be formed integrally on the silicon substrate. In drug or chemical delivery systems, sensors and/or stimulation circuitry for sensing or inducing neural and other response can be formed directly in the silicon substrate which contains the microchannel. The sensor is disposed in close proximity to the chemical distribution nozzle, facilitating neural and other studies. Microvalve arrangements can be formed with the microchannel, controlled by the on-chip circuitry.

14 Claims, 6 Drawing Sheets

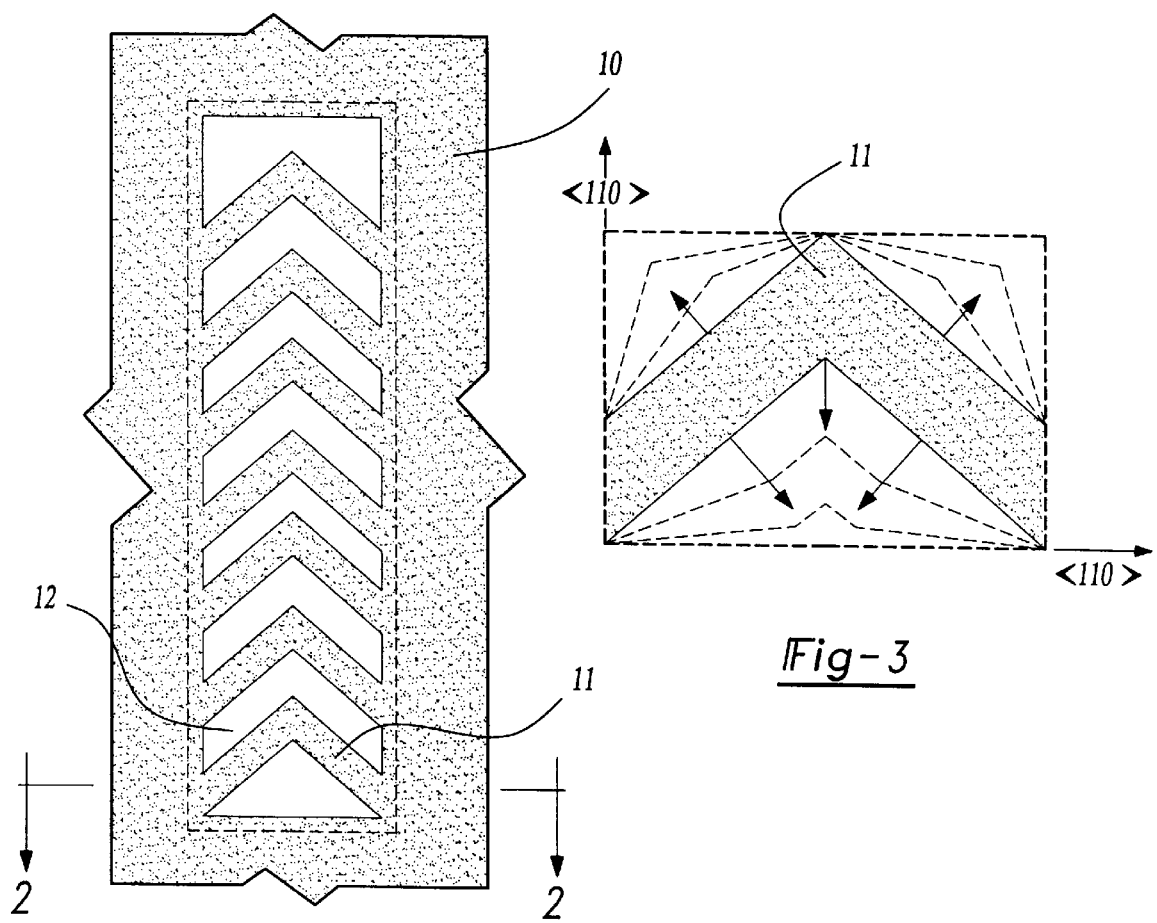
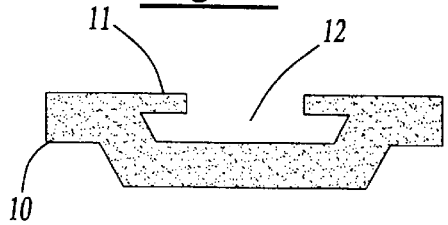
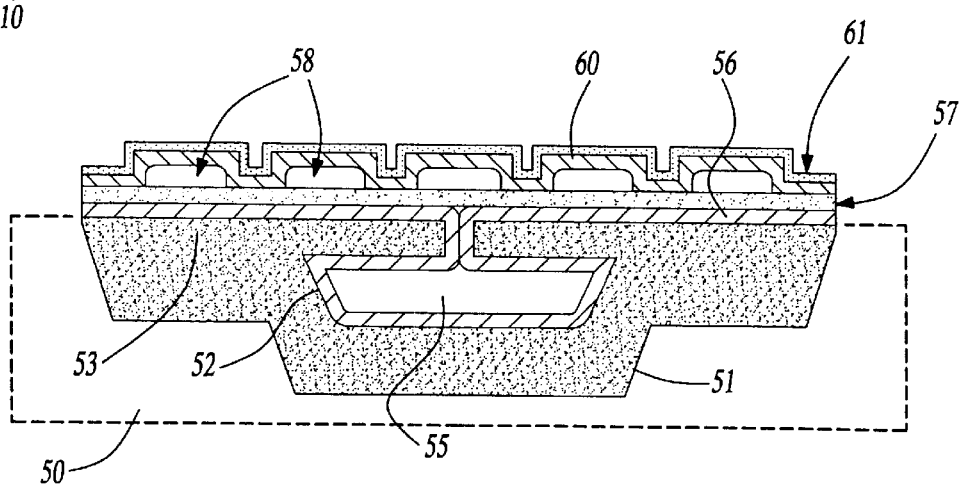

MICROCHANNEL SYSTEM FOR FLUID DELIVERY

This application is a divisional of copending application application Ser. No. 08/489,069 filed on Jun. 9, 1995.

GOVERNMENT RIGHTS

This invention was made in part using federal funds from the Neural Prosthesis Program, under Contract No. NIH-NINDS-N01-NS4-2303. The government may have certain rights in the invention.

BACKGROUND OF THE INVENTION

1. Field of the Invention

This invention relates generally to microchannel arrangements, and more particularly, to a system for forming microchannel structures, particularly for the delivery of drugs, chemical to agents, inks, and other fluids, with very high precision.

2. Description of the Related Art

There are a number of technological areas where it is desired to deliver a fluid with high spatial precision. In one area of technology, ink jet printers seek to place drops of ink on a page by propelling the ink out of small equally-spaced nozzles. Such printers generally are less is expensive and quieter while printing than laser printers. However, their printing quality is generally not as good as that of laser printers, partially as a result of shortcomings in the nozzle structures currently being used. The realization of a low-cost high-resolution nozzle array is critical to the future of ink jet printers.

Presently, nozzle arrays made of glass fibers are widely used. Such nozzle heads are highly uniform and quite robust. They generally are fabricated by aligning cord fibers, assembling fiber arrays, and then bonding the glass array to supporting glass plates. In order to achieve the required precision in aligning the nozzles, notched structures made of silicon or glass are generally used as a supporting substructure. The spacing between neighboring notches and the wall thickness of the cord fibers become the main factors limiting the separation between the nozzles.

Another problem that is associated with glass nozzle heads is in the wiring that connects same to the host computer. Glass nozzles do not permit the direct integration of circuitry on-chip. Without addressing circuitry, each nozzle requires a separate wire for controlling the firing of the ink. Large numbers of wires cause a tethering problem, limiting the number of nozzles on a print head. A print head with only 10 to 60 nozzles then has to move across the paper being printed many times to print a single page. This results in slow printing speeds compared to other approaches.

In another technological area, it is well-known that complex biochemical reactions are the underlying mechanism on which the functionality of the nervous system is based. In order to understand better the behavior of biological neural networks, at the circuit level, it is important to be able to deliver drugs or other chemicals to highly localized areas of neural tissue in precise quantities while monitoring the responses in vivo. By way of example, specific caged molecules, such as calcium, can be delivered to influence cellular behavior, and NMDA (n-methyl-d-aspartate) can be delivered to modify synaptic activity. In these applications, it is important that the injecting device be very small so as not to disturb the neural system and that it be able to inject fluid volumes in the range of 10–1000 pl controllably.

The most commonly used techniques for injecting chemicals into brain tissue have been microiontophoresis and pressure-injection using single-barrel and multiple-barrel glass micropipettes. The responses of nearby neurons are then measured using separately positioned pipettes filled with electrolyte. These approaches typically suffer from relatively poor control in positioning the injecting pipette relative to the monitoring points. Additionally, the complicated procedures required for the assembly of multiple-barrel pipette structures also prevent them from being widely used. There is, therefore, a need for a neural drug-delivery probe that is able to deliver chemicals selectively at the cellular level as well as being able to record electrically from, and stimulate, neurons, in vivo. Such a probe should allow detailed studies of the neural responses to a variety of chemical stimuli, and would represent an important step toward improving scientific understanding of neural systems and treating a variety of neurophysiological disorders.

In the applications noted hereinabove, as well as others, there is a need for a microchannel nozzle arrangement wherein drive, sensor, and/or control circuitry can be combined with the nozzle. Such an integration of the nozzle or nozzles with associated integrated circuitry cannot be achieved with structures formed of quartz, or where the microchannel structure is constructed on top of a substrate, as this not only makes the overall structure larger, but also renders same incompatible with the use of the same area for forming associated circuitry and/or electrodes.

It is, therefore, an object of this invention to provide a system for forming a microchannel for the delivery of a fluid with very high precision, illustratively with a spatial selectivity on the order of 60 $\mu$m or less.

It is another object of this invention to provide a system that achieves spatially selective fluid delivery and that is compatible with on-chip control systems.

It is also an object of this invention to provide a system that achieves spatially selective drug delivery and that is compatible with on-chip recording and stimulation systems.

It is a further object of this invention to provide an ink jet print head system.

It is additionally an object of this invention to provide an ink jet print head system that employs a silicon substrate having thereon on-chip drive systems.

It is yet a further object of this invention to provide a high resolution ink jet printing system.

It is also another object of this invention to provide an ink jet print head having multiple flow channels in a high nozzle density arrangement.

It is yet an additional object of this invention to provide a system in which plural microcapillary tubes are fabricated using lithographic processes.

It is still another object of this invention to provide a system in which a microcapillary tube is formed on a silicon wafer and combined with on-chip electronics.

It is a yet further object of this invention to provide a system in which a microcapillary tube is formed on a silicon wafer with dimensional control on the order of ±1 $\mu$m and combined with on-chip structures such as heaters, microvalves, and integrated electronics.

It is also a further object of this invention to provide an ink jet printing head arrangement that can achieve printing resolution greater than 1000 dots per inch (dpi).

It is additionally another object of this invention to provide an ink jet printing head arrangement that can be fabricated, with heaters, using just five masks.

A still further object of this invention is to provide a microchannel arrangement wherein fluid flow therethrough can precisely be determined.

SUMMARY OF THE INVENTION

The foregoing and other objects are achieved by this invention which provides, in a first device aspect thereof, a microchannel nozzle arrangement for conducting and expelling a fluid. In accordance with the invention, a silicon substrate having a top surface is provided with a longitudinal channel formed therein. A channel seal is arranged to seal the top surface of the silicon substrate, and to overlie the longitudinal channel. Thus, the longitudinal channel is embedded in the silicon substrate.

In one embodiment, the channel seal is formed of a plurality of cross structures that are formed integrally with the silicon substrate. Each such cross structure is arranged to overlie the longitudinal channel, the cross structures being arranged sequentially thereover. In a preferred embodiment, each of the cross structures has a substantially chevron shape.

A first seal over the longitudinal channel is achieved by oxidizing at least partially the cross structures, whereby the spaces between them are filled. In a further embodiment, a dielectric seal is arranged to overlie the thermally oxidized cross structures, thereby forming a more complete seal and a substantially planar top surface to the silicon substrate. In one practical embodiment of the invention, the dielectric seal is formed of a low pressure chemical vapor deposition (LPCVD) dielectric layer.

In an embodiment of the invention wherein it is desired to expel the fluid from the microchannel nozzle by application of heat, as is the case in ink jet printing, a heater is arranged to overlie the dielectric seal. A current passing through the heater causes a corresponding increase in the temperature of the fluid, which may be an ink, and same is caused to be expelled out of the microchannel. It is significant in such an embodiment that the material which forms the seal be thermally conductive, in order that the heat from the heater be transferred to the fluid within the microchannel nozzle.

In one highly advantageous embodiment of the invention, control circuitry for operating the heater can be formed integrally on the silicon substrate. Such control circuitry will include other circuit structures, such as bonding pads and sensors.

In embodiments of the invention where highly precise drug or chemical delivery is desired to be achieved, sensors and/or stimulation circuitry for sensing or inducing neural and other cellular responses can be formed in the silicon substrate. Such proximity of the sensor circuitry to the drug distribution nozzle facilitates placement of the sensor in close proximity to the chemical distribution nozzle, thereby solving a significant problem with prior art systems.

In some embodiments of the invention, microvalve arrangements can be formed in connection with the microchannel, and under the control of the on-chip circuitry.

In a practical embodiment of the invention, there is additionally formed in the silicon substrate a reservoir with a fluid conduit for coupling the fluid reservoir with the longitudinal channel. Thus, after expulsion of the fluid from the microchannel nozzle, the microchannel is replenished, illustratively by capillary action.

As will be described hereinbelow, the silicon substrate is formed, at least partially of boron-doped silicon. Preferably the boron-doped silicon is configured as a boron-doped silicon layer that is formed by boron diffusion. An initial diffusion can be rather shallow, illustratively on the order of 3 $\mu$m, and such a boron-doped layer will resist etching as the channel is formed.

In accordance with a further device aspect of the invention, a microchannel nozzle array is formed in a silicon substrate having a top surface having a plurality of channels formed therein. Each such channel has a plurality of cross structures integrally formed therewith and arranged to overlie each of the longitudinal channels. The cross structures are arranged sequentially over the longitudinal channel. A channel seal is arranged to seal the top surface of the silicon substrate and to overlie the plurality of longitudinal channels.

In one embodiment of the invention, the cross structures each have a substantially chevron shape. However, the invention is not limited to this configuration. Any of several configurations which are disposed diagonally, or at a significant angle, with respect to the channel can be employed in the practice of the invention. Additionally, the silicon substrate is provided with a boron-doped portion in the vicinity of the longitudinal channels. The longitudinal channels are formed by a silicon etching process which is resisted by the boron-doped cross structures. Thus, the etching process proceeds beneath the cross structures. Thus, as previously described, when the cross structures are subjected to thermal oxidation, the spaces therebetween are filled-in. Also, a dielectric layer is applied thereover, further ensuring that a seal is achieved.

Basically, as long as the opening through the shallow boron-doped silicon layer is composed of a line-shaped array with the lines oriented along the <100> direction of silicon crystal orientation, the subsequent wet etch in EDP will result in a continuous flow channel substantially along the <110> direction. Such openings in the array may be in the shape of a chevron, in the form of a straight line oriented substantially along the <100> direction, in the form of a network composed of chevron shape and line segment oriented substantially along the <100> direction, or any network composed of line segments oriented substantially along the <100> direction. It is additionally important that a planar wafer surface be produced which is compatible with conventional fabrication of heaters, electrodes, and circuits. The process of the present invention can be used at the front end of a conventional probe fabrication process, as a first mask. Conventional processes can be employed after the sealing of the microchannels is performed.

It is a significant aspect of the present invention that a boron diffusion be performable through the grating, in order that subsequent etching be permitted from the back of the wafer. Such etching from the back of the wafer is necessary to form a free-standing device.

As previously stated, each of the longitudinal channels can be provided with an associated heater, each heater overlying one of the longitudinal channels. Also, control circuitry for controlling the operation of the heaters can be formed integrally in the silicon substrate. The fluid that is expelled by the microchannel nozzles is replenished by capillary action from a fluid reservoir that is itself formed integrally with the silicon substrate. A fluid conduit arrangement couples the fluid reservoir with each of the longitudinal channels.

In accordance with a method aspect of the invention, a method of forming a microchannel nozzle includes the steps of:

performing a boron-diffusion to form a boron-doped layer on the surface of a silicon wafer;

first etching the boron-doped layer on the surface of a silicon wafer to form a plurality of sequential structures, the members of which are oriented at a significant angle with respect to the <110> directions of the silicon wafer;

second etching beneath the sequential structures to form a longitudinal channel thereunder; and first sealing the longitudinal channel by thermally oxidizing the sequential structures, whereby oxidized silicon closes the spaces between the sequential structures.

In one embodiment of this method aspect of the invention, the step of boron diffusion is performed on a p-type silicon wafer, and in a preferred embodiment is performed to form a highly doped boron diffusion having a thickness of approximately 3 µm.

The step of first etching, in one embodiment, includes the step of performing a reactive ion etch. Such an etching process forms the boron-doped sequential structures in the surface of the silicon wafer. In a preferred embodiment, the sequential structures have a chevron shape, however, the invention is not limited to this shape. The sequential structures are then subjected to an anisotropic silicon etch (e.g., EDP), which is resisted by the boron-doped sequential structures. Etching occurs beneath the sequential structures so long as they are significantly misaligned with the <110> material axes, such that a channel is formed embedded in the silicon wafer. The channel is oriented in the <110> direction, and is covered by the sequential structures. In some embodiments of the invention, the channel thus formed is subjected to a further boron diffusion. This is a deep boron diffusion which will dope the probe, including the silicon below the microchannel, to allow subsequent formation of a freestanding device. Thermal oxidation and deposited chemical vapor deposited dielectrics can be used to close the gaps in the grate to seal the channel. If outlet orifices are needed, either the chevron gaps can be increased so they are not sealed by the dielectrics or they can be reopened later using a selective (masked) etch through the dielectrics and the silicon. When they are later opened, the problems associated with spinning photoresist over the non-planar orifices are avoided.

After the microchannels are sealed, the upper surface of the dielectrics over the channels can be highly planar, and therefore, leads for recording and stimulating sites can be formed using conventional techniques.

BRIEF DESCRIPTION OF THE DRAWING

Comprehension of the invention is facilitated by reading the following detailed description, in conjunction with the annexed drawing, in which:

FIG. 1 is a schematic top plan view of a microchannel formed in accordance with the invention showing chevron-shaped cross structures;

FIG. 2 is a schematic cross-sectional representation taken along line 2—2 in FIG. 1;

FIG. 3 is a schematic representation that illustrates the extent and direction of the progress of the etching which forms the microchannel beneath the chevron-shaped cross structures;

FIG. 5 is a schematic cross-sectional representation of a microchannel structure useful as a microprobe for delivering a chemical agent to local volumes of tissue;

DETAILED DESCRIPTION

The realization of a buried flow channel in silicon in accordance with the present invention, depends upon the anisotropy of the silicon etch rate in EDP. For example, the (100) plane has an etch rate that is about 50 times faster than that of the (111) plane. Another consideration that is important in the practice of the present invention is that highly boron-doped single crystal silicon with a doping concentration higher than $7 \times 10^{19}$ cm$^{-3}$ is not significantly attached in EDP. Thus, if highly boron-doped silicon is used as an etch mask, and an opening perpendicular to the <100> direction is cut through this layer to expose the (100) plane, a subsequent wet etch in EDP will undercut the mask to form a continuous flow channel.

FIG. 1 is a top plan schematic representation of a silicon wafer 10 having a plurality of cross structures 11 arranged to overlie a channel 12. In this specific embodiment, cross structures 11 are each configured to have a chevron shape.

FIG. 2 is a cross-sectional representation of silicon wafer 10 in FIG. 1, taken along line 2—2. As shown, a cross structure 11 overlies channel 12.

Figure 4:
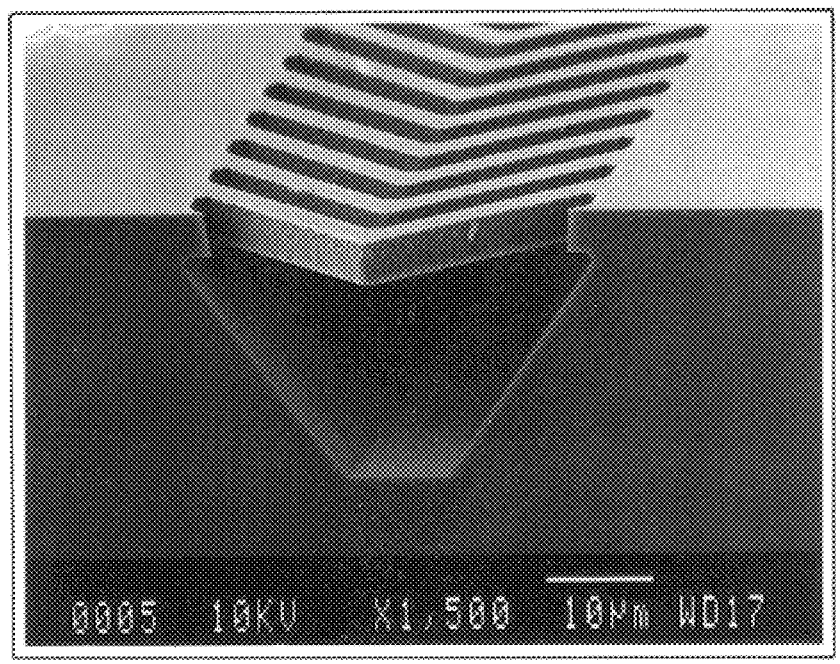
FIG. 4 is a micrograph that illustrates the cross-section of an etched microtube after undercutting of the silicon chevron pattern in an anisotropic silicon etch (EDP)

FIG. 3 is a schematic representation of a cross structure 11, further showing the direction and progress of the anisotropic etch over time. This figure additionally shows the directional orientation of the mask with respect to structure of the silicon wafer. FIG. 4 is a micrograph showing an actual silicon wafer etched as previously described. This micrograph was taken at a magnification of 1500 and shows a corresponding 10 µm distance.

FIG. 5 is a schematic cross-sectional representation of a microflow structure that is useful as a microprobe capable of delivering chemical agents to local volumes of tissue. The present invention enables the delivery of drugs to very local areas of tissue, especially in conjunction with electrical recording and/or stimulation. The present invention achieves the significant advantage of enabling injection of chemical agents with a spatial selectivity of less than approximately 50 µm on a chronic basis, and to perform simultaneous electrical recording and stimulation. Structures of this type are useful in pharmacological studies and in therapies to suppress certain neurological disorders, such as epilepsy.

The probe of the present invention is formed with microchannels embedded in a boron-doped substrate, so as to form a hollow core probe. As described, at the beginning of the probe formation process, a shallow boron diffusion is used to dope the probe substrate area everywhere and then a mask is used to etch through the boron layer to form a chevron pattern as described. When the wafer is exposed to an anisotropic silicon etch, the etch will undercut the chevron shaped cross structures to form a straight-sided (<110>) groove with the shallow boron-doped silicon over the top of the groove, thus forming a microchannel. The chevron-shaped cross structures thus form what appears as a grate. The etchant does not attack boron-doped silicon and attacks along the <100> directions in the substrate much faster than along the <111> directions. The wafer is then subjected to normal deep boron diffusion, that will dope the probe in a conventional way, including the silicon below the microchannel. As will be described, thermal oxidation and chemical vapor deposited dielectrics can be used to close the gaps in the grate to seal the channel. Where outlet orifices are needed, either the chevron gaps can be increased so that they are not sealed by the dielectrics, or they can be reopened later using a selective masked etch through the dielectrics and the silicon. As previously noted, this avoids problems which are associated with spinning photoresist over the non-planar orifices.

After the microchannels are sealed, the upper surface of the dielectrics over the channels are highly planar, and therefore, leads for recording and stimulating sites can be run thereover.

FIG. 5 illustrates a cross-section of a microprobe wherein a host silicon substrate 50 has a probe substrate 51 formed therein. The probe substrate has a substrate region 52 and a cross structure region 53, both of which are formed of p$^{++}$ silicon. The substrate and cross structure regions enclose a flow channel 55 which is sealed by a combined LPCVD and thermal oxide layer 56. As shown, LPCVD/thermal oxide layer 56 closes the gap in cross structure 53, and also coats the interior of the flow channel.

In this specific embodiment, the LPCVD/thermal oxide layer is covered by a silicon nitride layer 57 and relieves the compressive stress that would otherwise be present in the composite structure. A plurality of electrode conductors 58 are shown deposited on silicon nitride layer 57, and are themselves coated with an LPCVD oxide layer 60. The entire structure is then, in this specific embodiment, coated with an LPCVD silicon nitride layer 61. The sequence of the LPCVD oxide and nitride layers (57/57 and 60/61) can be reversed, as convenient in processing.

Figures 6, 7:
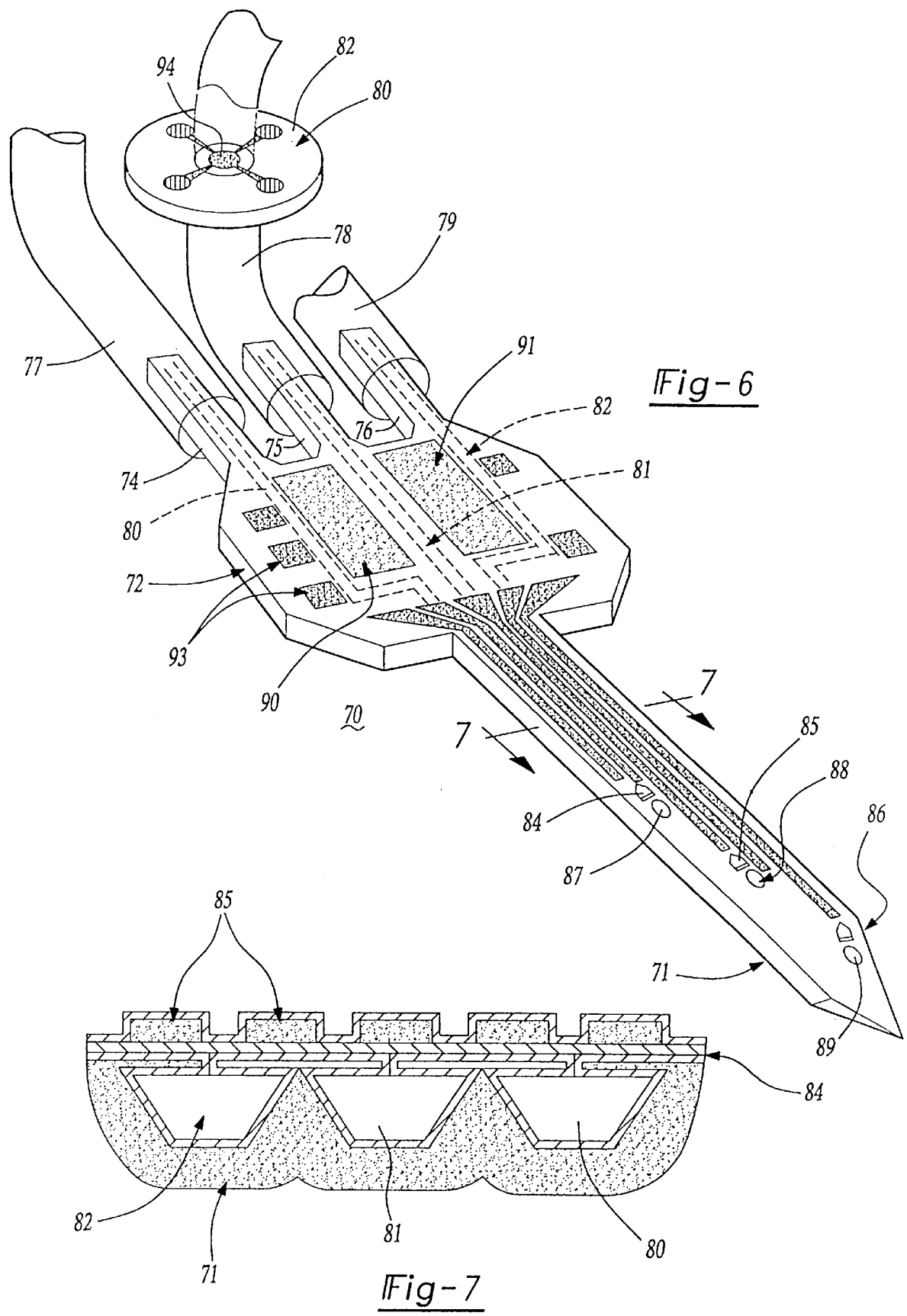
FIG. 6 is an isometric representation of a three channel micromachined drug-delivery probe.
FIG. 7 is a schematic representation of a cross-section of the drug-delivery probe shown in FIG. 6, taken along line 7—7 therein.

FIG. 6 is a schematic isometric representation of a three-channel drug-delivery probe 70, constructed in accordance with the invention. As shown, drug-delivery probe 70 has a probe portion 71 and a body portion 72 that are integrally formed with one another. Body portion 72 additionally has formed therewith, in this embodiment, three inlets, 74, 75, and 76. The inlets are coupled to respective supply tubes, that are shown as polyimide pipettes 77, 78, and 79. In certain embodiments of the invention, the rate of fluid flow through the polyimide pipettes can be monitored with the use of respective flow sensors, such as flow sensor 80 which is of the hot-wire type. The flow sensor has a mesh structure 81 formed by a polysilicon heater suspended across a hole in a substrate 82, which may be created by masking a boron-doping used for shank definition from the area under the intended mesh. When fluid flows through the mesh, it cools the structure, changing the resistance of the polysilicon, and thereby providing an indication of the flow rate.

In this embodiment, three microchannels 80, 81, and 82, are coupled respectively to inlets 74, 75, and 76. The microchannels continue from body portion 72 and extend along probe portion 71 where they are provided with respective outlet orifices 84, 85, and 86. Each such outlet orifice has arranged, in the vicinity thereof, a respective one of electrodes 87, 88, and 89. These electrodes are coupled to integrated circuitry shown schematically as integrated CMOS circuits 90 and 91 which are coupled to bonding pads 93.

FIG. 7 is a cross-sectional representation of drug-delivery probe 70 taken along line 7—7 to of FIG. 6. The elements of structure are correspondingly designated. As shown in FIG. 7, drug-delivery probe 70, in its probe portion 71, has microchannels 80, 81, and 82 embedded therein, and have a LPCVD/thermal oxide layer 84 arranged thereover. A plurality of electrode conductors 85 are arranged over the LPCVD/thermal oxide layer, substantially as described hereinabove with respect to FIG. 5.

Figure 8:
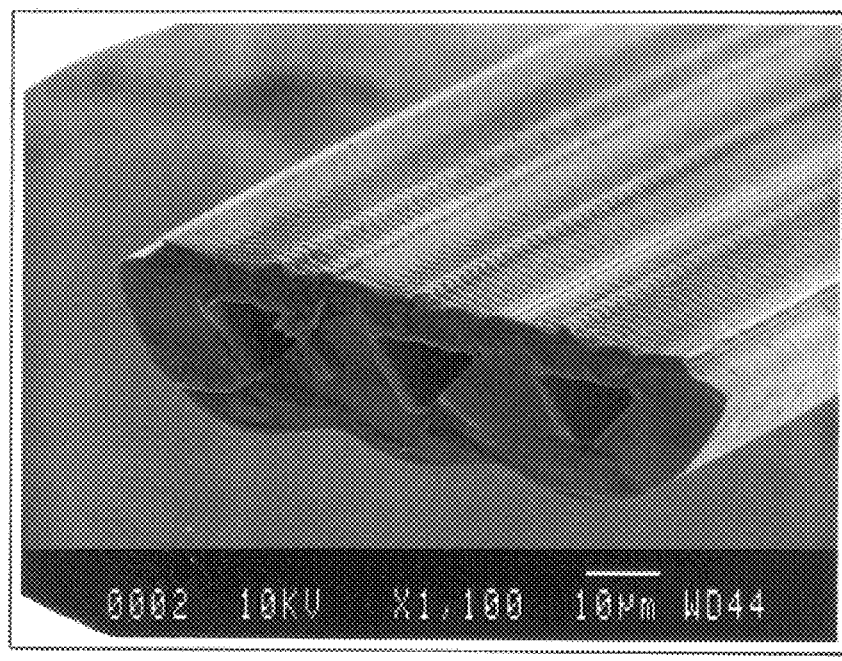
FIG. 8 is a cross-sectional representation of a three barrel microprobe showing polysilicon interconnections for electrical recording and stimulating electrodes.

FIG. 8 is a micrograph showing a cross-section of a three-barrel microprobe, similar to that described herein with respect to FIGS. 6 and 7. The micrograph of FIG. 8 shows the polysilicon interconnect for electrical recording and stimulating electrodes arranged over the flow channels.

As shown with respect to FIGS. 6–8, the inventive structure buries multiple flow channels in the probe substrate, resulting in a hollow core device. The upper surface of the probe is therefore planar and can accommodate electrode structures. Fabrication of the microchannels begins with a shallow boron diffusion to form a 3 µm thick highly boron doped layer on the surface of a p-type (100) silicon wafer. The intended channel is then opened through this layer in the form of a chevron pattern using a reactive ion etch (RIE), and an anisotropic silicon etch (EDP) is used to undercut this chevron structure to form a flow tube aligned with <110> direction, as shown in FIGS. 1–4. A deep boron diffusion is then performed to define the probe shank. Sealing of the channel is accomplished using thermal oxidation, LPCVD deposited dielectrics, and an optional planarizing etch-back. Multichannel arrays with channel-to-channel separations as small as 4 µm can be achieved. The inventors herein have constructed microprobes with one to four flow channels, channel widths having been varied from 10 µm to 32 µm, while the probe shanks widths range from 58 µm to 74 µm. As long as only a few flow channels are required, the flow tubes do not increase the overall width of the probe over conventional probes. The probes have a typical shank length of 4 mm, which is consistent with the targeted cortical systems. However, the invention is not limited to this shank length. The channel depths are controlled by etch time and by the lateral width of the channel opening, with depths of 10 µm being typical. At the back of the probe, the flow channels protrude from the body of the substrate to allow flexible pipette tubing to be sealed therearound, as described hereinabove with respect to FIG. 6. This tubing typically is approximately 60 µm in diameter with a 7 µm thick wall. The tubing is connected to a thermally-based flow sensor, such as flow sensor 80 in FIG. 6, and an external pump (not shown). The flow sensor is process compatible with the probe and may be fabricated on the same wafer.

After sealing of the microchannels is achieved, fabrication of the microprobe continues by depositing a polysilicon conductive layer and doping same with phosphorus. The polysilicon is then patterned by RIE followed by LPCVD oxide/nitride/oxide triple-layer passivation. The areas for the recording-stimulating sites, and bonding pads, are next opened using RIE, and chromium/gold is deposited in the openings and patterned using lift-off. Finally, the dielectrics outside the intended device are removed, and the fluid ports for the channels are opened using a masked etch.

A critical step in the fabrication process is the sealing of the channels. Improper sealing will result in cracking of the channel during subsequent high temperature processing. As described herein, the sealing process begins with a thermal oxidation. The growth of thermal oxide on the silicon beams spanning the channel will reduce the width of the chevron-shaped openings. As a result, the thicker the oxide has grown, the thinner the LPCVD dielectrics that are required to seal the channel. However, as the width of the chevron-shaped silicon beams is reduced, the thermal oxidation time becomes critical in determining the robustness of the channel structure. For very narrow beams, over-oxidation will convert all of the beam into oxide, making the sealing over the channel transparent. In this case, the membrane over the channel is prone to crack during subsequent high-temperature processing. This can be avoided by reducing the oxidation time to preserve silicon in the chevron bridge structure.

Figure 9:
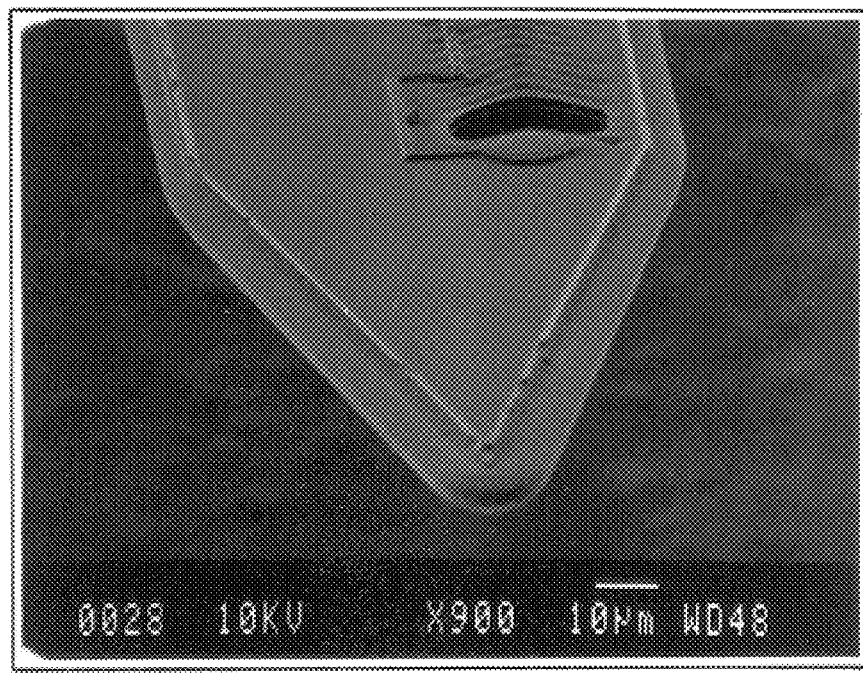
FIG. 9 is a microphotograph of the tip of a drug delivery neural probe of the type shown in FIG. 6.

FIG. 9 is a microphotograph showing an outlet orifice at the tip of the probe portion, as well as the recording/stimulating electrode. In this embodiment, the distance between the orifice and the electrode site is approximately 2.5 $\mu$m. In injecting chemicals using microprobes, knowledge of the friction losses in the microchannels is important in determining how much pressure should be applied to achieve a desired flow rate. The frictional losses associated with fluid flowing in a pipe depend on many factors, including the average velocity of pipe flow, the pipe diameter D, the fluid density $\rho$, the fluid viscosity $\mu$, and the average pipe wall roughness. From conventional fluid dynamics, for laminar flow, the product of Reynold's number $R_e$ and the Darcy friction factor $f$ is a constant which depends on the diameter of the pipe cross-section. The definition of Reynold's number $R_e$ and the Darcy friction factor $f$ are:

$$R_e = \rho V D / \mu$$
$$f = \frac{2D(\Delta p)}{\rho V^2 L}$$

where $\rho$ is the fluid density (996 kg/m³ for water at 23° C.), V is the cross-sectional average velocity of fluid in the pipe, D is the hydraulic diameter of the channel (4 times the cross-sectional area divided by the wetted perimeter length), $\mu$ is the viscosity of the fluid (for water, 9.85×10$^{-4}$ kg/m·sec at 23° C.), $\Delta p$ is the pressure drop across the channel due to friction losses, and L is the length of the channel.

In order to determine the frictional loss for fluid flowing in the microchannels, silicon chips with 2.15 cm long microchannels were fabricated. The upper width of the channels was kept at 40 $\mu$m (defined by the etch mask), while the channel depths varied from 14 $\mu$m to 17 $\mu$m. These dimensions were measured under an optical microscope by cleaving the chips after the experiments. The hydraulic diameter D of the channel could then be calculated. Distilled water was used for the measurements. Regulated nitrogen was applied through a cylindrical accumulator to pressurize the distilled water. Before entering the microchannel, the water was passed through a 0.45 $\mu$m filter to prevent blocking the microchannel. The pressure drop across the channel was measured using a differential pressure sensor. With the channel oriented horizontally and taking the water to be incompressible, the pressure drop resulted from frictional losses. The volumetric flow rate was determined by monitoring the movement of the water meniscus in a transparent constant cross-section micropipette. In order to minimize the influence of water evaporation on the measurement, a drop of vegetable oil was kept in the far end of the measuring pipette to form a buffer of air between the water meniscus and oil drop. In all measurements, the flow was assumed to be laminar and fully developed since $R_e$ is less than 1 and D/L is less than 10$^{-5}$. All measurements were performed at 21–23° C.

With the volumetric flow rate V and the pressure drop $\Delta p$ measured, the Reynold's Number $R_e$ and the Darcy friction factor $f$ can be calculated. The minimum flow rate was about 300 $\mu$m/sec, which is of the same order as the flow rates used with the chemical delivery probe. According to conventional fluid dynamics, for a normal-sized pipe of trapezoidal cross-section, the product of the Reynold's Number $R_e$ and the Darcy friction factor $f$ is about 60. From the experimental results conducted by the inventors herein, this product is more typically about 55 for a microchannel with a hydraulic diameter of 18 $\mu$m.

The foregoing results can be used to determine the pressure needed in the chemical delivery system to achieve the desired flow. If it is assumed that the volume of chemical to be injected is about 10% of the tissue volume normally monitored by a cortical recording electrode (about 100 $\mu$m³) and further assumed that the chemical must be injected in 1 second, then for an effective channel diameter of 10 $\mu$m, and a channel length of 4 mm, the required flow rate is 1.3 mm/sec and the required drive pressure is 11 Torr.

Intermixing is a natural phenomenon that occurs when two solutions are put in contact with one another. When a drug-delivering neural probe is being inserted into tissue, even without applied pressure on the external port of the microchannel, the drug will intermix with tissue fluid in the vicinity of the outlet orifice through diffusion. Using the one-dimensional form of Fick's diffusion equation, the interdiffusion of ions or molecules in such a solution can be described, and can be solved, using finite difference methods. As an example, assume the chemical stored in the microchannel is acetylcholine, and the volume to be injected is 100 pl. The diffusion coefficient of acetylcholine at 25° C. is 6.11×10$^{-6}$ cm²/sec. Further assuming that at time t=0, the acetylcholine and tissue fluid form an abrupt value at x=0; from x=–∞ to x=0, the channel is filled with acetylcholine, and from x=0 to x=+∞, a "virtual channel" is filled with tissue fluid. The relative amount of acetylcholine diffused into tissue is normalized by dividing by the intended dose $Q_s$. The result indicates that in approximately 141 minutes, the amount of acetylcholine diffused into tissue fluid is about the same as that of the intended injection. Although in a real situation, mixing may be influenced by cell membranes and by the finite dimensions of the channel, these preliminary results indicate that the influence of intermixing cannot be ignored, especially in chronic applications.

Figure 10:
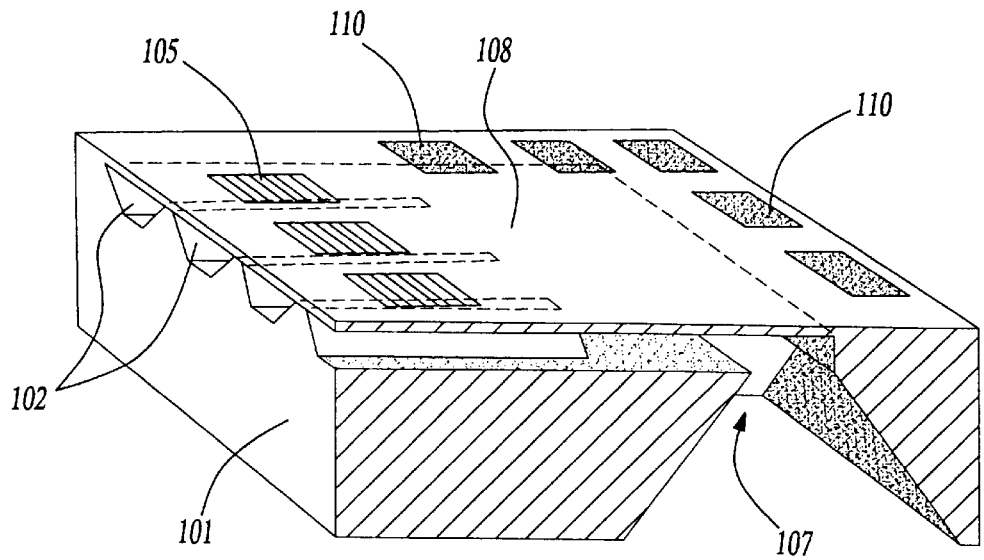
FIG. 10 is an isometric representation of an integrated silicon nozzle arrangement that is suitable for ink jet printing.

FIG. 10 is a schematic isometric representation of a monolithic silicon ink jet nozzle head 100. The nozzle head is formed on a silicon substrate 101 and is shown to have a plurality of nozzles 102 which are the outlet ports of associated microchannels, such as microchannel 104 which is shown cross-sectionally in the figure.

The particular nozzle head embodiment shown in FIG. 10 is intended as a nozzle head for ink jet printers, and accordingly, a plurality of polysilicon heaters 105 are each associated with a respective one of the microchannels and assist in expulsion of the ink (not shown) as will be described herein.

The ink is received at an ink inlet orifice 107 and fills a front-end ink reservoir 108. By means of channels, which are not shown in the drawing, the ink reservoir is coupled to each of the microchannels and, as will be described hereinbelow, capillary action causes the microchannels to be refilled with ink after ink expulsion. The ink is expelled by applying a current to polysilicon heaters 105 via a plurality of bonding pads 110.

The inventors herein have produced prototype nozzle arrays having 16 nozzles and a nozzle separation of 4 µm. One such prototype (not shown) has a 34 µm nozzle width and a corresponding printing resolution of 668 dpi. Another prototype nozzle array (not shown) has a nozzle width of 21 µm and a corresponding resolution of 1016 dpi. As previously indicated, after a drop of ink is ejected, the nozzle refills automatically from the front-end reservoir by capillary action. The reservoir, in a specific illustrative embodiment of the invention, measured approximately 1.5 mm×1 mm×20 µm in size. The ink, as indicated, is supplied via the ink inlet orifice which is in the form of a recess etched from the back of the wafer and connected, as stated, to the main ink reservoir (not shown).

The front-end reservoir is formed during the formation of the microchannel array. As previously mentioned, the area of the front-end reservoir is as large as 1.5 mm×1 mm while the width of each flow channel is no larger than 40 µm. The undercutting and sealing process mentioned hereinabove operates well for small areas, such as microchannels, but not for large areas, such as the reservoir. In high temperature (930° C.) sealing using LPCVD, the large-area reservoir ceiling is prone to cracking due to compressive forces in the ceiling mesh. In addition to the large dimensions, the sealing material is also of critical importance. For small area devices, such as the flow channels, as long as the silicon cross structures are preserved after thermal oxidation, LPCVD oxide, LPCVD nitride, or a combination of both, can be used for sealing the structure. However, for large area devices like the reservoir, stress and strain problems become more serous, and only LPCVD oxide can be used after thermal oxidation for the ceiling.

Another problem that gives rise to cracks in the reservoir ceiling comes from weak points in the boundary area connecting the microchannel array to the reservoir. The silicon ceiling network is prone to break here after undercutting the structure in EDP. All of these problems, however, can be solved using special structures in the ceiling design, and a robust device structure is achieved herein.

The fabrication of a nozzle head begins with the thermal oxidation of a (100) silicon wafer. The device area is then defined by a shallow boron diffusion on the front side of the wafer. Next, as previously described, chevron-shaped opening are cut through the boron-doped layer using reactive ion etching to define the nozzles and the front-end ink reservoir area. This layer is undercut by EDP to form the front-end reservoir and flow tubes aligned with the <110> direction. The ceiling of the undercut area is then sealed using thermal oxidation and LPCVD deposited dielectrics.

In the present specific embodiment, the microtubes are formed in parallel and connect to a common front-end ink reservoir, which is essentially a much wider tube. The next step is the formation of the heaters. In order to increase heat transfer to the ink, the dielectric layer under the polysilicon heaters should be as thin as possible. This is realized by thinning the sealing dielectrics using a dry etch before heater formation. Polysilicon heaters are then deposited using LPCVD, are doped with phosphorus, and are patterned. While some of the devices formed use polysilicon interconnects defined in the same material used for the heaters, other devices have used aluminum interconnects in order to reduce the resistance from the heaters to the bonding pads. After depositing and patterning the aluminum, low temperature oxide (LTO) and PECVD dielectrics are deposited for passivation. Areas for the bonding pads are then opened using reactive ion etching, and chromium/gold is inlaid in the vias and patterned using sputtering and lift-off.

On the back side of the wafer, the dielectric layer is patterned and a second EDP etch is used to open a hole. This hole works as an ink inlet orifice and connects to the front-end ink reservoir, as shown in FIG. 10. The exposed areas on the front side are covered by dielectrics or gold and are not attacked in EDP. Finally, the wafer is cut perpendicular to the tube orientation using a dicing machine to expose the nozzles, and the individual devices are released using similar cutting procedures.

Figure 11:
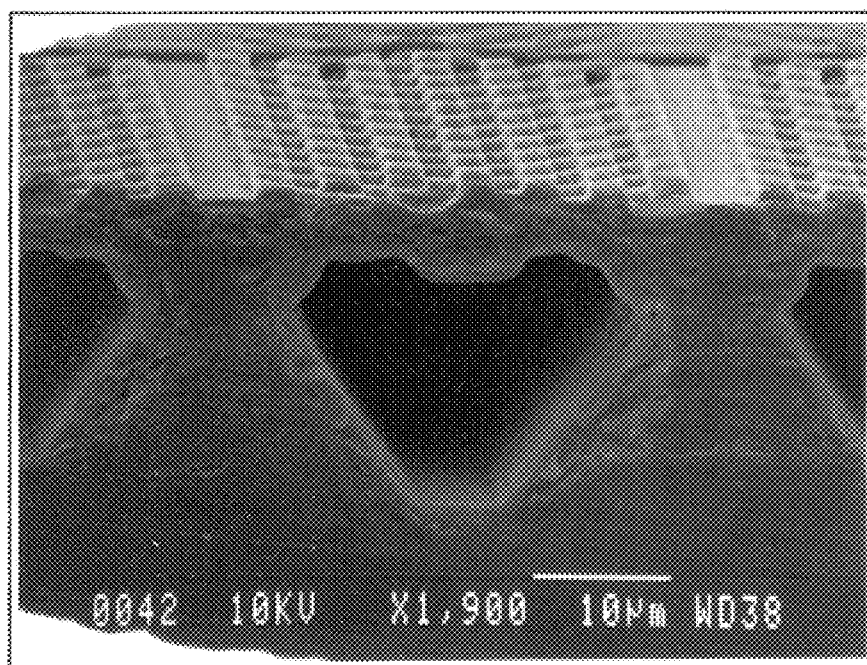
FIG. 11 is a microphotograph of a cross-section of a nozzle head showing the location of heaters formed from polysilicon resistors disposed on top of the microtubes.

FIG. 11 is a microphotograph showing a close-up of a print head constructed in accordance with the invention. The print head, in this embodiment, has 16 nozzles and a resolution of 1016 dpi.

In the nozzle array structure of the present invention, neat transfer efficiency to the ink is enhanced by the high thermal conductivity of the silicon structures in the channel ceiling, while the bulk silicon maintains high interchannel isolation. In order to evaluate thermal cross-talk in the array, a circuit analog which simulates the thermal characteristics of this ink-channel array system was employed. In this simulation, ink in the channel was divided into small elements representing 1 µm thick ink layers while the silicon channel structure was accurately depicted by equivalent thermal capacitors and resistors. For ink jet printing, the typical duration of the current pulse for triggering the heaters is between 2 µs and 6 µs. In this short time period, heat only propagates about 3 µm into the ink, and it is the temperature in the top skin layer of the fluid that determines the "ink explosion." The temperature at which the explosion starts is called the "super heat limit," which depends upon the chemical composition of the ink and ambient pressure. A typical value for the super heat limit is about 330° C. at atmospheric pressure for the ink used in some commercial ink jet print heads.

Figure 12:
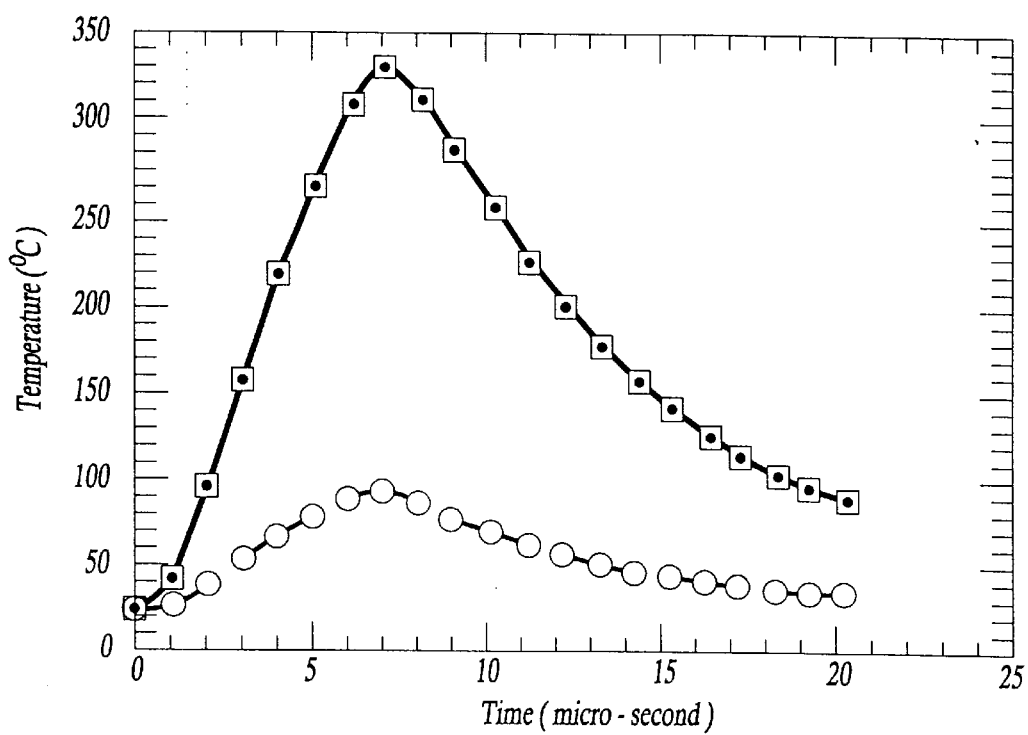
FIG. 12 is a graphical representation of simulated temperatures of the ink top skin layer produced when left and right channels on either side of a central channel are triggered by a 6 µs pulse.

When one of three consecutive microchannels in an array is activated by turning on its heater, not only will ink in this channel be heated, but ink in the neighboring channels will be heated as well. For the case where both the left and right channels are driven by a 6 µs wide current pulse, while the central channel is kept "quiet" (e.g., is not triggered), then, due to lateral heat conduction through the ceiling and the silicon substrate, the ink in the central channel will be heated, achieving its highest temperature in the top skin layer. FIG. 12 shows the simulated temperatures of the top skin layers of these channels versus time for a 6 µs wide current pulse applied at t=0. The figure shows the highest temperatures anywhere in the layers, which for the central channel occurs in the upper corner of the channel.

At time t=7 µs, the trigger channels achieve their super heat limit and ink is fired out of their nozzles. At the same time, the central channel is heated only up to 88° C. by lateral conduction. This temperature is well below the super heat limit and will not cause erroneous to firing. The simulations also show that the heat disturbances from channels other than the nearest neighbors are negligible.

In considering the maximum triggering frequency allowed in this device, it is initially assumed that all three channels are firing simultaneously. Before they cool down, the left and right channels fire again while the central channel is kept "quiet." In this case, the triggering pulse width is kept at 6 µs while the period of the signal is varied.

Figure 13:
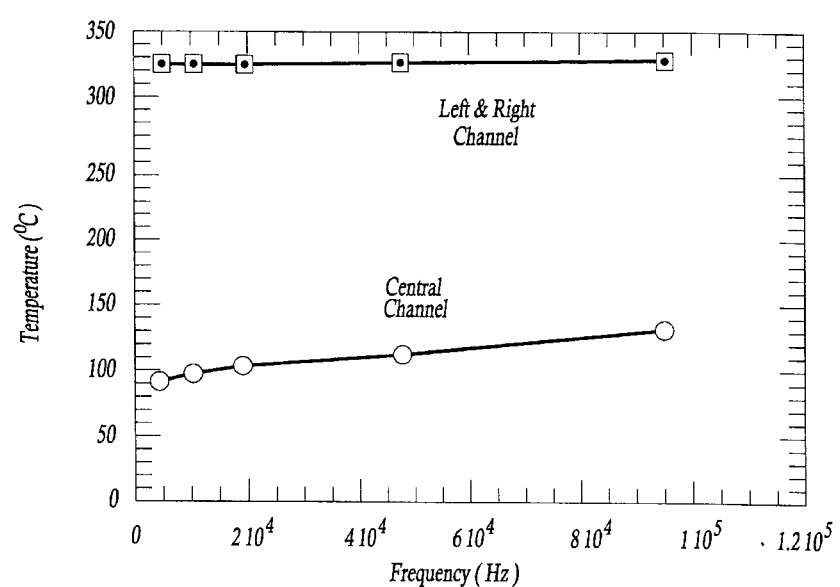
FIG. 13 is a graphical representation of simulated temperature of the ink top skin layer plotted against firing frequency.

FIG. 13 shows the simulated temperatures of the ink top skin layers versus firing frequency. Even at a firing frequency as high as 100 KHz, the temperature of the top skin layer in the central channel is heated to only 120° C., which is still below the minimum activation temperature. From these results, it is clear that thermal cross-talk is not a problem in this structure. It is the ink capillary re-filling speed and the speed of the stepper motor that will determine the maximum printer speed.

A prototype device was mounted on a PC board for testing. After being supplied through the inlet orifice, ink immediately filled the nozzle array by capillary action and was observed through a microscope. With the print head oriented horizontally and a piece of paper oriented vertically and spaced 2 mm from the nozzles, a current pulse of 20 $\mu$s wide and 16 ma in amplitude was sufficient to fire ink onto the paper. This corresponds to a heater power density of $3.35 \times 10^8$ W/m$^2$. The diameter of each dot is about 20 $\mu$m.

The fabrication of the device of the present invention requires only five masks and no wafer-to-wafer bonding. The fabrication process is also compatible with the addition of on-chip circuitry for multiplexing the heater control signals, thereby increasing the number of ink jet nozzles which can be provided on the print head, enhancing the printing speed, and realizing full page printing, while minimizing the external lead count.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A method of forming a microchannel nozzle, the method comprising the steps of:

performing a boron diffusion to form a boron-doped layer on the surface of a silicon wafer;

first etching the boron-doped layer on the surface of a silicon wafer to form a plurality of sequential structures;

second etching beneath the sequential structures to form a longitudinal channel thereunder; and first sealing the longitudinal channel by thermally oxidizing the sequential structures, whereby oxidized silicon reduces the size of the spaces between the sequential structures.

2. The method of claim 1, wherein said step of performing a boron diffusion is performed on a p-type silicon wafer.

3. The method of claim 1, wherein said step of performing a boron diffusion is performed to form a highly doped boron diffusion having a thickness of approximately 3 $\mu$m on a p-type silicon wafer.

4. The method of claim 1, wherein said step of first etching comprises the step of performing a reactive ion etch.

5. The method of claim 1, wherein said step of first etching comprises the step of forming a plurality of sequential structures arranged diagonal with respect to said longitudinal channel.

6. The method of claim 1, wherein said step of second etching comprises the step of performing an anisotropic silicon etch.

7. The method of claim 1, wherein, after performing said step of second etching, there is provided the further step of boron diffusing the longitudinal channel.

8. The method of claim 1, wherein there is further provided the step of second sealing the longitudinal channel by depositing a dielectric layer over the oxidized sequential structures.

9. The method of claim 8, wherein said step of second sealing comprises the step of depositing a LPCVD dielectric layer over the oxidized sequential structures.

10. The microchannel nozzle arrangement of claim 1, wherein said channel seal is formed of a thermally conductive material.

11. The method of claim 1, wherein there is further provided the step of forming a fluid reservoir in the silicon wafer.

12. The method of claim 1, wherein there is further provided the step of dicing the silicon wafer along a direction substantially orthogonal to the longitudinal channel to expose a nozzle formed of the longitudinal channel.

13. The method of claim 1, wherein there is further provided the step of forming a heater over the longitudinal channel.

14. The method of claim 1, wherein there is further provided the step of forming integrated control circuitry in said silicon wafer.

* * * * *